(12) United States Patent
Dall'Asta et al.

(10) Patent No.: US 6,458,973 B1
(45) Date of Patent: Oct. 1, 2002

(54) PROCESS FOR THE PREPARATION OF 5-CARBOXYPHTHALIDE

(75) Inventors: Leone Dall'Asta, Milan; Umberto Casazza, Turate; Giovanni Cotticelli, Cernusco sul Naviglio, all of (IT)

(73) Assignee: Norpharma S.p.A., Milan (IT)

( * ) Notice: Subject to any disclaimer, the term of this patent is extended or adjusted under 35 U.S.C. 154(b) by 0 days.

(21) Appl. No.: 09/690,301

(22) Filed: Oct. 17, 2000

(51) Int. Cl.[7] .................... C07D 305/12; C07D 307/76; C07D 407/00
(52) U.S. Cl. ........................................ 549/305; 549/307
(58) Field of Search ................... 549/305, 307

(56) References Cited

U.S. PATENT DOCUMENTS 3,607,884 * 9/1971 Forney ........................ 549/305

FOREIGN PATENT DOCUMENTS

| DE | 26 30 927 | 1/1978 | ................. 549/305 |
| WO | WO/00234311 | 4/2000 | ................. 549/305 |
| WO | WO 01/32642 A1 | 5/2001 | ................. 549/307 |
| WO | WO 01/32643 A1 | 5/2001 | ................. 549/307 |

OTHER PUBLICATIONS

Forney, Leroy S. et al.: "Reaction of Formaldehyde with Deactivated Benzoic Acids. An ester–directed electrophilic aromatic substitution process" J. Org. Chem. (1971), 36 (5), 689–93, XP002145376.

Forney, Leroy S.: "Reaction of Terephthalic Acid with Formaldehyde in sulfur Trioxide Media" J. Org. Chem. (1970), 35 (5) 1695–96, XP002145377.

J. R. Blanc et al., J. Org. Chem. 1961, 26, 4731–4733.

* cited by examiner

Primary Examiner—Alan L. Rotman
Assistant Examiner—Raymond Covington
(74) Attorney, Agent, or Firm—Kenyon & Kenyon

(57) ABSTRACT

There is described a process for the preparation of 5-carboxy phthalide, which comprises adding terephthalic acid to fuming sulfuric acid containing at least 20% of $SO_3$, then adding formaldehyde to the mixture, heating the mixture at a temperature of 120–145° C. and isolating 5-carboxyphthalide from the reaction mixture.

28 Claims, No Drawings

PROCESS FOR THE PREPARATION OF 5-CARBOXYPHTHALIDE

FIELD OF THE INVENTION

The present invention concerns a process for the preparation of an isobenzofuran derivative. More particularly, the invention refers to a process for the preparation of 1-oxo-1,3-dihydro-5-isobenzofurancarboxylic acid.

1-Oxo-1,3-dihydro-5-isobenzofurancarboxylic acid, hereinbelow simply also referred to as 5-carboxyphthalide, represented by the formula A,

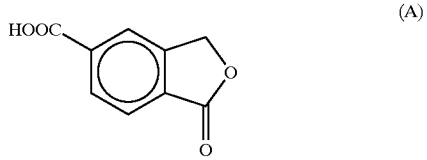

is a useful intermediate in the preparation of several chemical compounds, particularly dyes, resins and drugs. In particular, 5-carboxyphthalide is an intermediate useful in the synthesis of citalopram, a well-known antidepressant drug, whose preparation using said intermediate is described in the International Patent Application WO 00023431 and in the corresponding Italian Patent Application IT1999 MI 0001724, whose contents are incorporated by reference herein.

BACKGROUND OF THE INVENTION

It is known that 5-carboxyphthalide may be prepared by reduction of one of the carbonyl groups of trimellitic anhydride, which can occur by hydrogenation or, according to DE-2630927, by electrochemical reduction. This method has the drawback of giving a 5-carboxyphthalide containing, as a by-product, the 6 isomer in an amount which can reach 10%. An impurity which is present in such a percent cannot be accepted if 5-carboxyphthalide must be used as an intermediate in the preparation of drugs and, in such a case, it must be removed or strongly reduced to a value not higher than 0.1%. The removal of the 6 isomer occurs by several crystallizations which lower the yield in final product considerably.

It is also known that 5-carboxyphthalide may be prepared according to another method, described in U.S. Pat. No. 3,607,884, which comprises reacting terephthalic acid with formaldehyde in liquid sulfur trioxide ($SO_3$). This synthesis must be carried out very cautiously whereby it is not suitable for the industrial scale-up owing to the problems connected to the use of liquid sulfur trioxide. More particularly, according to this method, it is needed to use small volumes of $SO_3$ and to try to maintain a sufficient fluidity of the reaction mixture. Nevertheless, the reaction mass remains in any case thick and, therefore, involves a difficult handling for the recovery of the end product.

Furthermore, it is known (J. R. Blanc et al., J. Org. Chem. 1961, 26, 4731–4733) that isophthalic acid reacts with formaldehyde in oleum to give 3,3', 5,5'-tetracarbomethoxydiphenylmethane. According to this document, by heating at 119° C. a mixture of 0.2 mol of isophthalic acid and 0.1 mol of 95% paraformaldehyde in 100 ml of oleum containing 20% of $SO_3$, the 3,3', 5,5'-tetracarbomethoxydiphenylmethane is obtained in a 14% yield.

It is advisable to have a process that allows the synthesis of 5-carboxyphthalide with high yield and purity and easily controllable in the industrial scale.

Finally, it is known (L. R. S. Forney et al., J. Org. Chem. 1971, 36, 689–693) that a mixture of terephthalic acid, formaldehyde and oleum containing $SO_3$, when heated at 150° C. for 2 hours in a sealed tube, may give good conversion rates of terephthalic acid to 5-carboxyphthalide, the best coversion being achieved at a 60% $SO_3$ concentration. However, according to this method, 5-carboxy phthalide is not isolated and said conversion rate is calculated after esterification with methanol and determination of the 5-carboxy phthalide methyl ester thus obtained by gas chromatography.

Reaction conditions like these, however, are not suitable for the industrial scale because pressure reactors and strong acidity conditions are required.

SUMMARY OF THE INVENTION

It has now surprisingly found that, by addition of terephthalic acid to fuming sulfuric acid (oleum) containing at least 20% of $SO_3$, by subsequent addition of formaldehyde to the mixture and by heating, 5-carboxyphthalide is obtained in good yields and in a high degree of purity under easily controllable conditions, in open and however not pressurized reactors, and without any risk in handling the reaction mixtures.

Thus, the present invention provides, according to a method of simple execution, a process for the preparation of 5-carboxyphthalide of formula A, which comprises adding terephthalic acid of formula I

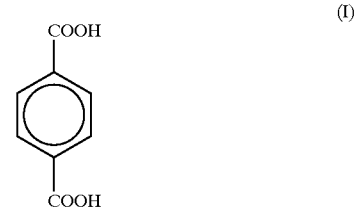

to fuming sulfuric acid containing al least 20% of $SO_3$, subsequently adding formaldehyde thereinto, heating the mixture at 120–160° C. and isolating the obtained 5-carboxyphthalide.

DETAILED DESCRIPTION OF THE INVENTION

According to a preferred embodiment of the process of the present invention, formaldehyde is used in one of its solid forms, currently in form of its precursor 1,3,5-trioxane of formula II

in about equimolecular amounts in respect of the starting terephthalic acid, preferably corresponding to 2.5–3.2 mol of formaldehyde/mol of terephthalic acid.

The fuming sulfuric acid, which represents the reaction medium, also is the dehydrating agent which allows the direct transformation, in situ, of the 2-hydroxymethylterephthalic acid thus obtained of formula III

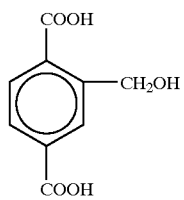

(III)

into 5-carboxyphthalide of formula A.

In practice, terephthalic acid is added to fuming sulfuric acid, currently containing at least 20%, advantageously 22–33%, preferably 25–30% of $SO_3$, then the mixture thus obtained is treated with 1,3,5-trioxane at a temperature of 30–35° C. and subsequently heated at a temperature of 120–145° C., preferably at 130–135° C. Generally, it is sufficient to heat to 120° C. so that the temperature of the reaction mixture increases by spontaneous exothermia up to 130–135° C. Preferably, after having reached 120° C., it is suitable to wait about 15 minutes in order to verify whether such exothermia has occured. In the negative, the temperature is brought to 130–145° C. and, after a 2–5-hour heating at this temperature, there is formed compound III which concurrently dehydrates to give 5-carboxyphthalide. The preferably used amount of fuming sulfuric acid containing 25–30% in $SO_3$ is 2–8 l/Kg of terephthalic acid, advantageously 2–6 l/Kg, preferably 3–6 l/Kg, particularly about 3 l/kg.

The advantage of the process of the present invention in comparison with known methods is that to give the 5-isomer of carboxyphthalide selectively. From the reaction mixture, which may contain some residual $SO_3$, 5-carboxyphthalide is isolated according to methods known in the art.

Thus, for example, when the reaction is over, the mixture may be poured into ice, by anyhow controlling the exothermia of this operation, and the strong acidity of the medium may be neutralized with a base, preferably sodium hydroxide, carbonate or bicarbonate.

At the end of the reaction the mixture in sulfuric acid may also at first be diluted with glacial acetic acid and then treated with water. In such a case, advantageously, the mixture is diluted with glacial acetic acid in an amount of 200 ml per 100 g of terephthalic acid, by letting the temperature to rise to 20–25° C. at the end of the addition. Successively the water is added and, under external cooling, the temperature may rise to 45° C. Finally, the mixture is neutralized with a base, as set forth above.

In the isolation steps, during the addition of the base, it may be suitable to reach a pH≅8, whereby the 5-carboxyphthalide is present in the solution as a salt, advantageously of an alkali metal, preferably of sodium, and to filter off the insoluble products whilst the 5-carboxyphthalide salt remains dissolved in the medium. In such a filtration it is suitable to use a neutral filter aid, for example Celite® or Dicalite®. The 5-carboxyphthalide free acid may be easily recovered in good yields from the solution containing its salt by neutralization with an acid, for example with hydrochloric acid, and isolated in sufficiently pure form for its use as intermediate for the preparation of drugs. Practically, the 5-carboxyphthalide precipitates at acid pH at a value of about 3, preferably in the range of 1.8–3.0, and is isolated by simple filtration. In the isolation steps through the salt, preferably with an alkaline metal, it is suitable to maintain the pH value not higher than 8 in order to avoid the formation of by-products. Furthermore, during the treatment with the alkaline agent, it is suitable to control the pH changes when a value of about 5 is reached, because around this value it is possible that small additions of base involve considerable pH variations.

Alternatively, at the end of the reaction the mixture may be treated by dropping water thereto, so that said water initially destroys any possible residual $SO_3$ and then dilutes sulfuric acid progressively thus rendering the isolation of 5-carboxyphthalide easier. The addition of water, which produces exothermia, is preferably made at a temperature of 0–5° C. However, the control of the temperature may be limited to the initial period of the addition of 10–15% of water (in respect of the used fuming sulfuric acid); afterwards, particular care are not necessary because the temperature of the mixture remains at about 20–25° C. and, hence, it may be easily controlled. The 5-carboxyphthalide may be isolated by simple filtration, by washing with water, if necessary by triturating the obtained product in water.

The following examples illustrate the invention without, however, limiting it.

EXAMPLE 1

To 800 ml of fuming sulfuric acid, containing about 27% of $SO_3$, 260 g (1.56 m) of terephthalic acid are added, under stirring, in 15 minutes and without exceeding the temperature of 25° C. To the thick suspension thus obtained, 120 g (1.33 m) of 1,3,5-trioxane are added under stirring without exceeding the temperature of 35° C., then stirring is continued for 20–30 minutes without cooling, whereby the temperature of the mixture rises to 45–50° C. The mixture is heated to 120° C. and it is noted that, already at 90° C., the mass becomes clear whilst at 120° C. a light exothermia is observed which brings the temperature to 135–140° C. The mixture is kept 6 hour under stirring at this temperature, then it is cooled to 20° C. and poured in 3000 g of coushed ice without exceeding the temperature of 25° C. To the mixture thus obtained, a 15% w/w solution of sodium hydroxide is added to a pH≅6 (about 6500–7000 ml thereof are needed), by keeping the temperature at 35–40° C. by water-cooling, then a 5% w/w solution of sodium hydroxide is added thereto at the temperature of 35–40° C. up to pH≅8 (about 300 ml are needed). The solid is removed by filtration on Dicalite® in a buchner and washed with water. To the filtered solution thus obtained, 35% hydrochloric acid is added up to pH≅1 (requiring about 1600–1800 ml of 35% HCl) and the suspension thus obtained is heated to 35° C. The solid is filtered, washed 3 times with 500 ml of deionized water at 40° C. and suspended in 1000 ml of deionized water. The suspension is heated under stirring at 50–55° C. and kept 1 hour under these conditions, then it is hot filtered. The solid is washed with deionized water and dried in vacuo at 50° C. to constant weight. Thus, 180 g of light-brown coloured 5-carboxyphthalide with a purity (HPLC) >95% are obtained.

EXAMPLE 2

To 800 ml of fuming sulfuric acid, containing about 27% of $SO_3$, 260 g (1.56 m) of terephthalic acid are added, under stirring, in 15 minutes without exceeding the temperature of 25° C. By maintaining the stirring, 60 g (0.665 m) of 1,3,5-trioxane are added portionwise to the thick suspension thus obtained, whereby the temperature rises to bout 25° C. The mixture is cooled to 10–15° C. in 30 minutes, then a further 60 g (0.665 m) of 1,3,5-trioxane is added thereinto. The mixture is heated and it is observed that at 90° C. the mass becomes clear. The temperature is brought to 120° C. and the mixture is kept 10–15 minutes under these conditions, whereby the temperature may rise to 135–140° C. If no exothermia is observed, the mixture is nevertheless heated to 130–135° C. and kept 4 hours under these conditions. The cooled mixture is poured, in about 1 hour and without exceeding the temperature of 25–35° C., into 3000 g of crushed ice. To the mixture thus obtained, 8000–8500 ml of a 15% w/w solution of sodium hydroxide are added to a pH=5–6, by letting the temperature to rise to 35–40° C. and by keeping it at these values by a water-cooling. Then, at 35–40° C., 300 ml of 5% w/w solution of sodium hydroxide are added to the mixture to a pH≅8. The solid is removed by filtration on a Dicalite® bed in a buchner and washed with water. To the solution thus obtained, 2000 ml of 35% hydrochloric acid are added to a pH≅1 and the suspension thus obtained is heated to 35° C. The solid is filtered, washed 3 times with 500 ml of deionized water at 40° C. The wet product is treated with 4000 ml of warm deionized water (about 45° C.) and the suspension is heated 30 minutes under stirring at 45° C. Without cooling, the product is filtered, washed with deionized water and dried in vacuo at 50° C. to constant weight. Thus, 215–225 g of light-brown coloured 5-carboxyphthalide with a purity (HPLC) >95% are obtained.

EXAMPLE 3

To 153 ml of fuming sulfuric acid, containing about 27% of $SO_3$, 50 g (0.3 m) of terephthalic acid are added, under stirring, at room temperature, then 23 g (0.25 m) of 1,3,5-trioxane are added thereinto in two portions, by cooling to a temperature of 15–18° C. after any addition. At the end of the addition, the mixture is left 30 minutes under stirring at room temperature, then it is heated at 135–145° C. and let under stirring for 2–2.5 hours at this temperature until the end of the reaction. The reaction mixture is cooled to a temperature lower than 3° C., then 100 ml of glacial acetic are added thereto by keeping the temperature at about 25° C. At the end of the addition, the mixture is let to stand 60 minutes under stirring at 20–25° C. and filtered. The wet product is suspended in 1900 ml of water. The suspension is heated up to 25–30° C. under stirring, its pH is adjusted to about 8 by gradual addition of 175 g of sodium bicarbonate. The solid is filtered off on Celite® by washing with hot water (40–45° C.). The pH of the mother liquors is brought to 1.5 by addition of about 125 ml of 37% hydrochloric acid and the obtained precipitate is filtered at 20–25° C. by washing with water until the filtrate reaches a neutral pH. Thus, 32 g of 5-carboxyphthalide with a titer (HPLC) >93% are obtained.

EXAMPLE 4

To 892 g of fuming sulfuric acid, containing 25–27% of $SO_3$, 100 g (0.6 m) of terephthalic acid are added at 20–23° C., under stirring, then 46 g (0.5 m) of 1,3,5-trioxane are added portionwise thereto at about 15° C. At the end of the addition, the mixture is heated 2 hours at 130–133° C. whereby a dark, clear solution is obtained. When the reaction is complete, as shown by a HPLC control, the mixture is cooled to 20–22° C. and 210 g of glacial acetic acid are slowly added thereto, without exceeding the temperature of 23–25° C. The mass is cooled to −5–0° C. and 1800 ml of cold deionized water are added thereto. During this operation the temperature rises to 43–45° C. At the end of the addition, the mixture is kept 1 hour under stirring at 23–25° C., then it is filtered, the solid is washed with deionized water abundantly and suspended, still wet, in 1200 ml of deionized water at room temperature. To the suspension thus obtained, about 1550 g of a 7% solution of $NaHCO_3$ are added to a constant pH of 7,6–7,8. The mixture is filtered on Celite®, washing with deionized water. The pH of the filtrate is brought to about 1 by slow addition of about 120 ml of 35% hydrochloric acid at 22–25° C. The suspension is kept 1 hour under stirring at 22–25° C., then it is filtered and washed with deionized water abundantly. The product is dried in vacuo at about 50° C. to give 81 g of 5-carboxyphthalide with a titer (HPLC)>94% and purity (HPLC)>95%.

EXAMPLE 5

To 153 ml of fuming sulfuric acid, containing 25% of $SO_3$, 50 g (0.3 m) of terephthalic acid are added, in small portions, at 20–22° C., then to the mixture thus obtained 23 g (0.25 m) of 1,3,5-trioxane are added portionwise thereinto. The mixture is kept about 30 minutes under stirring, without cooling, then the temperature is brought to 135–140° C. and heating is continued for 2–2.5 hours, whereby the reaction is complete, as shown by a HPLC control. The reaction mixture is cooled to 0–2° C. and 1000 ml of cold water are added thereto without exceeding 20–23° C., by keeping in mind that, during the addition of the first 15–20 ml of water, exothermia occurs, whilst afterwards the temperature may be easily controlled. The mixture is kept 1 hour under stirring at 20–25° C., the product thus obtained is filtered, still moist triturated in 300 ml of water repeatedly until the reddish colour of the mother liquors disappears. After the third trituration, the pH of the mother liquors stabilizes at values ranging from 5 to 6. The product is dried in vacuo at 45–50° C. until constant weight to give 47.5 g of 5-carboxyphthalide with a titer and a purity (HPLC)>95%.

EXAMPLE 6

In a 3000-1 glass lined reactor, 550 Kg of oleum containing 25% of $SO_3$ are charged under vacuum and good aspiration, then, consecutively, under stirring, 56 Kg of terephthalic acid at 20–23° C. and 26 Kg of 1,3,5-trioxane at 15–20° C. are added thereinto. The reactor is heated at 130–133° C. for 4 hours, then the mixture is cooled to 20–23° C. and 118 Kg of glacial acetic acid are couled portionwise thereinto at a temperature not higher than 25° C. At the end of this operation, 1000 Kg of water are added portionwise, whereby the temperature is maintained not higher than 43–45° C. by circulation of water in the jacket. The mixture is stirred for about 1 hour at 20–23° C., then the product is centrifugated, squeezed and abundantly washed with water in order to remove the larger amount of sulfuric acid from the mother liquors and to obtain 100–105 Kg of 5-carboxyphthalide as a well squeezed, wet raw-product. In a 3000-1 stainless steel reactor the product thus obtained is suspended in 680 Kg of deionized water and a solution of 60 Kg of sodium bicarbonate in 540 Kg of deionized water is then slowly added to said suspension to a pH of 7.0–7.2. To the solution thus obtained, lightly cloudy, 10 Kg of Celite® are added, the solid is filtered off and the solution, at a temperature of 22–25° C., is brought to pH=3 with 32% hydrochl 20–22° C. and centrifugated. The product is well squeezed, abundantly washed with deionized water and dried under vacuum to give 41–43.7 Kg of 5-carboxyphthalide.

What is claimed is:

1. A process for the preparation of 5-carboxyphthalide of formula A

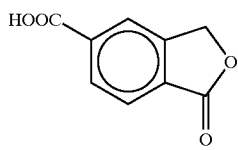 (A)

which comprises adding formaldehyde and terephthalic acid of formula I

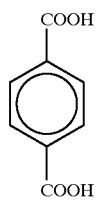 (I)

to fuming sulfuric acid containing at least 20% of $SO_3$, heating the mixture at 120–145° C. and isolating the 5-carboxyphthalide thus obtained.

2. A process according to claim 1, in which formaldehyde is used in form of its precursor 1,3,5-trioxane of formula II

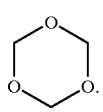 (II)

3. A process according to claim 1, in which formaldehyde is used in form of its precursor paraformaldehyde.

4. A process according to claim 2, in which the 1,3,5-trioxane of formula II is used in an amount corresponding to 2.5–3.2 mol of formaldehyde/mol of the starting terephthalic acid.

5. A process according to claim 4, in which said 1,3,5-trioxane is added at a temperature of 30–35° C.

6. A process according to claim 1, in which the fuming sulfuric acid contains 22–33% of $SO_3$.

7. A process according to claim 6, in which the fuming sulfuric acid is used in an amount of 3–6 liters/Kg of terephthalic acid.

8. A process according to claim 7, in which fuming sulfuric acid is used in an amount of about 3 liters/Kg of terephthalic acid.

9. A process according to claim 1, in which 5-carboxyphthalide is isolated by neutralization of the reaction mixture with a base.

10. A process according to claim 1, in which 5-carboxyphthalide is isolated by diluting the reaction mixture with glacial acetic acid, then adding water and neutralizing with a base.

11. A process according to claim 9 or 10, in which said base is an alkaline metal base.

12. A process according to claim 11, in which said alkaline metal base is sodium hydroxide, carbonate or bicarbonate.

13. A process according to claim 1, in which, at the end of the reaction, the 5-carboxyphthalide is isolated by the formation of a solution containing a salt thereof which is neutralized with an acid.

14. A process according to claim 13, in which said salt is the sodium salt.

15. A process according to claim 13, in which the salt is formed by adding the base to a pH of about 8.

16. A process according to claim 13, in which said acid is hydrochloric acid.

17. A process according to claim 1, in which 5-carboxyphthalide is isolated by treatment of the reaction mixture with water.

18. A process according to claim 17, in which the addition of water is made at 0–5° C. and the exothermia is controlled by keeping the temperature at about 20–25° C.

19. A process according to claim 1, in which the mixture is heated at 130–135° C.

20. A process according to claim 1, in which formaldehyde is added to fuming sulfuric acid after the addition of terephthalic acid.

21. A process for the synthesis of citalopram, in which a process for the synthesis of 5-carboxyphthalide according to claim 1 is contained.

22. The process of claim 1 wherein the process is conducted in an open, non-pressurized reactor.

23. A process for the preparation of 5-carboxyphthalide of formula A

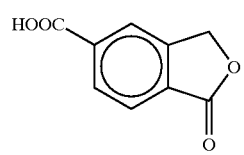 (A)

which comprises adding formaldehyde (or a formaldehyde precursor) and terephthalic acid of formula I

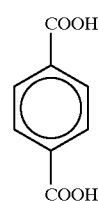 (I)

to fuming sulfuric acid containing at least 20% of $SO_3$, heating the mixture at 120–145° C. and isolating the 5-carboxyphthalide thus obtained, wherein the process is conducted in an open, non-pressurized reactor.

24. A process for the synthesis of citalopram, comprising the process for the synthesis of 5-carboxyphthalide according to claim 23.

25. Citalopram which has been produced by a process comprising the process for the synthesis of 5-carboxyphthalide according to claim 23.

26. A process according to claim 1, in which the mixture is heated at 120–130° C.

27. A process according to claim 23, in which the mixture is heated at 120–130° C.

28. The process of claim 1 wherein the process is conducted in a non-pressurized reactor.

* * * * *

UNITED STATES PATENT AND TRADEMARK OFFICE
CERTIFICATE OF CORRECTION

PATENT NO.    : 6,458,973 B1
DATED         : October 1, 2002
INVENTOR(S)   : Leone Dall'Asta et al.

It is certified that error appears in the above-identified patent and that said Letters Patent is hereby corrected as shown below:

<u>Title page,</u>
Item [30], insert -- [30] Foreign Application Priority Data
Jan. 18, 2000   (IT)   Italy ......M12000A  000050 --.

Signed and Sealed this

Twenty-fifth Day of March, 2003

JAMES E. ROGAN
*Director of the United States Patent and Trademark Office*

Disclaimer

6,458,973 B1 — Leone Dall'Asta, Milan (IT); Umberto Casazza, Turate (IT); Giovanni Cotticelli, Cernusco sul Naviglio (IT). PROCESS FOR THE PREPARATION OF 5-CARBOXYPHTHALIDE. Patent dated October 1, 2002. Disclaimer Filed February 10, 2012, by the assignee, Norpharma SPA.

Hereby disclaims and dedicates to the public, claims 1-28 and the entire term of the said patent.
(*Official Gazette, April 10, 2012*)